United States Patent [19]

Nayar

[11] Patent Number: 5,763,401
[45] Date of Patent: Jun. 9, 1998

[54] STABILIZED ALBUMIN-FREE RECOMBINANT FACTOR VIII PREPARATION HAVING A LOW SUGAR CONTENT

[75] Inventor: Rajiv Nayar, Richmond, Calif.

[73] Assignee: Bayer Corporation, Berkeley, Calif.

[21] Appl. No.: 678,492

[22] Filed: Jul. 12, 1996

[51] Int. Cl.$^6$ .............. C07K 1/00; A61K 35/16; A61K 38/00; A61K 38/16
[52] U.S. Cl. .............. 514/12; 514/21; 530/383
[58] Field of Search .............. 530/383; 514/12, 514/21

[56] References Cited

U.S. PATENT DOCUMENTS

| 4,440,679 | 4/1984 | Fernandes et al. | 530/383 |
|---|---|---|---|
| 4,623,717 | 11/1986 | Fernandes et al. | 530/383 |
| 4,758,657 | 7/1988 | Farb et al. | 530/383 |
| 4,847,362 | 7/1989 | Mathews et al. | 530/383 |
| 4,877,608 | 10/1989 | Lee et al. | 514/21 X |
| 5,288,853 | 2/1994 | Bhattacharva et al. | 530/383 |
| 5,328,694 | 7/1994 | Schwinn | 530/383 |
| 5,399,670 | 3/1995 | Bhattacharya et al. | 530/383 |
| 5,565,427 | 10/1996 | Freudenberg | 530/383 |

*Primary Examiner*—Cecilia J. Tsang
*Assistant Examiner*—P. L. Touzeau
*Attorney, Agent, or Firm*—James A. Giblin

[57] ABSTRACT

A stable albumin-free Recombinant Factor VIII (rFVIII) formulation in lyophilized form having both crystalline and amorphous components and comprising, when reconstituted with water, about 65 to 400 mM glycine, up to 50 mM histidine, 15 to 60 mM sucrose, up to 50 mM NaCl, up to 5 mM CaCl$_2$ and 50 to 1500 IU/ml of rFVIII. A very preferred formulation comprises upon reconstitution with water about 290 mM glycine, 20 mM histidine, 30 mM sucrose, 30 mM NaCl, 2.5 mM CaCl$_2$ and 50 to 1500 IU/ml of rFVIII. The residual water content of the lyophilized preparation is about 1 to 3% by weight, preferably about 1% by weight.

6 Claims, 1 Drawing Sheet

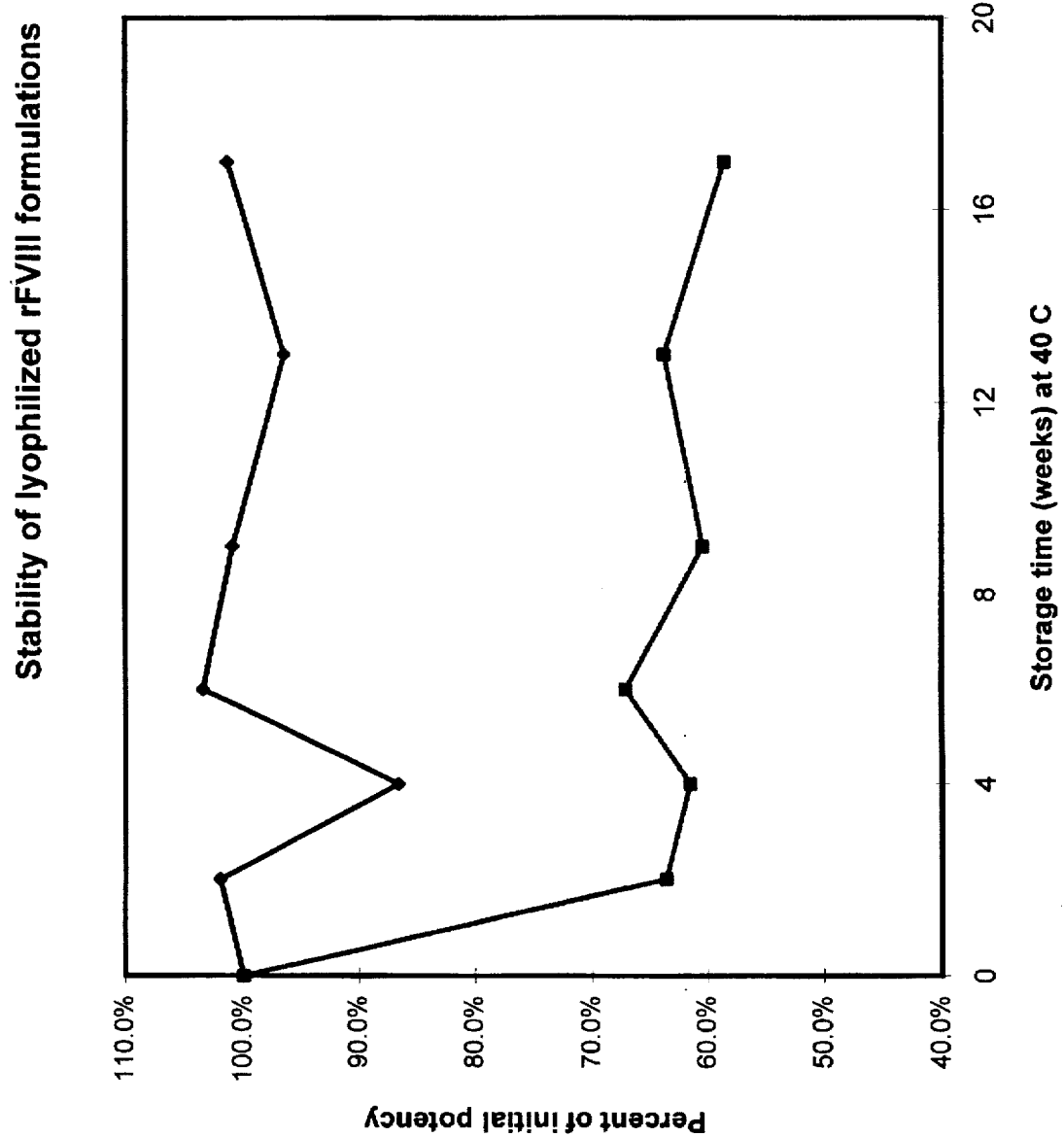

STABILIZED ALBUMIN-FREE RECOMBINANT FACTOR VIII PREPARATION HAVING A LOW SUGAR CONTENT

BACKGROUND OF THE INVENTION

1. Field

This application relates generally to pharmaceutical formulations and particularly to a lyophilized formulation for rFVIII which is stabilized without albumin (albumin-free).

2. Prior Art

Factor VIII is a well known plasma protein that is essential to the blood clotting process. Although Factor VIII can be and currently is obtained from human plasma, efforts have been made in recent years to manufacture Factor VIII from recombinant sources (rFVIII) to avoid potential contaminations associated with blood products. In addition, a recombinant source for Factor VIII provides a virtually unlimited supply of the coagulation factor, thus avoiding supply limitations associated with using donated blood plasma as a source material.

Since one of the advantages of a rFVIII product is that it is not derived from human plasma and thus avoids potential contamination from a human plasma source, it has been a goal in rFVIII manufacturing to develop a stable formulation for rFVIII which can be described as being entirely free of any human source raw materials. Unfortunately, however, rFVIII is a labile protein and, like many other therapeutic proteins, it can become unstable during storage. To overcome such instability, it has been common practice to include human serum albumin to the product as a stabilizer. Albumin has been found to be a good stabilizer of FVIII and is used in numerous commercial products on market. By using human albumin as a rFVIII stabilizer, however, one of the advantages of having a recombinant product in the first place (i.e., avoiding any human based source materials) is lost.

There have been some recently described albumin-free formulations for Factor VIII in both low and high ionic strength media using sodium chloride, calcium chloride and histidine as a buffer ion. In addition, basic amino acids such as lysine and sugars such as mannitol, sucrose or maltose have been used. To achieve stability in an albumin-free Factor VIII formulation while retaining necessary isotonicity needed for therapeutic use, approximately 10% sugar has been used in such albumin-free formulations. See for example U.S. Pat. No. 4,877,608 (low ionic strength formulation). European patent 0 314 095 discloses another albumin-free formulation having a high ionic strength and histidine as a buffering agent. The '608 patent is concerned with a liquid solution and not a lyophilized product that must be able to undergo freeze drying cycles necessary to prepare the product. European patent 314 095 includes a relatively high amount of sodium chloride and is primarily used in a liquid formulation.

Other patents concerned with Factor VIII formulations include U.S. Pat. No. 5,399,670, which describes the use of arginine in an albumin containing freeze dried formulation. See also WO 95/01804 which describes a formulation that includes no sucrose or glycine and U.S. Pat. No. 4,440,679 and U.S. Pat. No. 4,623,717 (both to Fernandes et al.) showing the use of at least 30% by weight sugars in combination with amino acids to stabilize FVIII in the liquid state under pasteurization conditions (60° C., at least 10 hours).

In addition to the above Factor VIII formulations there are several other patents related to the purification and/or stabilization of Factor VIII. These include U.S. Pat. No. 5,288,853 which covers a multi-step manufacturing process including the use of a heparin-coupled column followed by the addition of glycine to form a purified Factor VIII product.

U.S. Pat. No. 5,399,670 covers a process for producing a lyophilized Factor VIII preparation of enhanced solubility which requires addition of arginine to the Factor VIII solution prior to lyophilization.

U.S. Pat. No. 5,259,951 covers a multi-step method of purifying Factor VIII from plasma using ion exchange columns.

U.S. Pat. No. 4,758,657 covers a multi-step process for separating Factor VIII:C from plasma in which at least one of the steps requires the adsorption of Factor VIII:C on a hydrophobic interaction matrix.

In addition to the above patents, there is a very recently described formulation for Factor IX (FIX) which appears similar to the formulation for rFVIII disclosed herein. See Abstract 244 by L. Bush et al., Hemophilia, Vol. 2, Supplement 1, p. 64 (June, 1996). FIX is a pro-enzyme that is converted to an active proteolytic enzyme. FVIII serves, on the other hand, as a co-factor along with other coagulation components in effecting blood coagulation. The molecular weight of FVIII is about 340,000 Daltons whereas FIX has a molecular weight of about 56,000 to 57,000. FVIII is very sensitive to proteolytic processing with concomitant loss of coagulant activity. It is well known that Factor VIII is inherently more unstable than FIX and freeze dried concentrates of each factor demonstrate marked differences in stability on storage at various temperatures. Unlike FVIII, FIX includes unique gamma carboxylation of 12N terminal glutamic acid residues, thus providing a possible basis for differential stability. Thus a formulation for FIX would not necessarily suggest a formulation for FVIII.

In Pharmaceutical Research, Volume 12, No. 6, pages 831–837, 1995, there is also disclosed a formulation for stabilized recombinant human interleukin-1 receptor antagonist similar to that disclosed below.

Despite the past and recent efforts to develop a stable rFVIII preparation that can be successfully lyophilized and later reconstituted rapidly in water, to date it has been difficult to provide a formulation that not only avoids the use of human products such as albumin but also meets the requirements for proper lyophilization and rapid reconstitution and isotonicity while at the same time providing a rFVIII having long term stability, with a pharmaceutically acceptable shelf-life.

To our surprise we have now found that such a preparation is possible. In the course of developing this formulation, we found that histidine which has been taught and used in the prior art as a buffering agent, actually had a de-stabilizing effect on lyophilized albumin-free formulations. We have found however that the de-stabilizing effects of histidine can be effectively overcome by a novel formulation of salts, glycine and sucrose, the combination of which was found to have a beneficial effect in stabilizing rFVIII. This mixture also protects the rFVIII across multiple freeze thaw cycles during the lyophilization process, and it provides rapid reconstitution of the lyophilized product with water. The formulation includes both crystalline and amorphous components, unlike most prior art formulations which are essentially amorphous. The formulation of our invention remains stable in the liquid state for at least twenty-four hours at room temperature. Details of our formulation and its use are described below.

SUMMARY OF THE INVENTION

Our improved rFVIII formulation is a pharmaceutically acceptable albumin-free lyophilized product which can be rapidly reconstituted in water (within 30 seconds) and is suitable for treating hemophilia. The lyophilized preparation comprises a novel mixture of salts, amino acids and sucrose. The product is stable at room temperature and, unlike the prior art the formulations, comprises a relatively low level of sugar.

The formulation comprises, when reconstituted with water, the following ingredients:

glycine about 65 to 400 mM, preferably 290 mM, histidine up to about 50 mM, preferably 1 mM to 50 mM, very preferably 20 mM, sucrose about 15 to 60 mM, preferably 30 mM, NaCl up to about 50 mM, preferably 1 mM to 50 mM, very preferably 30 mM, $CaCl_2$ up to about 5 mM, preferably 0.1 to 5 mM, very preferably 2.5 mM, and rFVIII about 50 to 1500 IU/ml.

In a preferred lyophilized formulation, the amount of residual water should be about 1 to 3% by weight, preferably about 1% by weight.

BRIEF DESCRIPTION OF THE FIGURE

The figure is a graph comparing the potency over time at 40° C. of the formulation of this disclosure having a relatively low sugar content (upper curve) with a formulation taught by the prior art having a relatively high sugar content (lower curve).

DETAILED DESCRIPTION OF THE INVENTION

The objective that led to this invention was to identify an albumin-free formulation that offered stability to rFVIII (minimal or less than about 20% loss in potency) across various process steps such as ultrafiltration/diafiltration, storage of frozen bulk, freeze-thaw effects and lyophilization. In addition, a fast dissolving product was desired with stability in the reconstituted liquid state. Finally, a pharmaceutically acceptable lyophilized product with an appropriate shelf-life was desired which could be lyophilized with a short freeze-drying cycle.

Proteins do not crystallize during lyophilization. The goal of a drying process should be to convert the aqueous protein solution into an amorphous phase to protect the proteins from chemical and/or conformational instability caused by a crystalline (or total lack of water) environment. Thus, it is common to include significant amounts of albumin (up to 1%) to provide an amorphous phase (component) to stabilize the proteins.

Based on the overall objectives, a formulation with both a crystalline component to allow rapid lyophilization and an amorphous component to stabilize the rFVIII was developed. As used herein the expression crystalline with an amorphous component means that the formulation comprises two or more distinct phases at least one of which is crystalline and one of which is amorphous. Solids can exist in crystalline or amorphous form. Crystalline materials are characterized as having defined structure, stoichiometric compositions, and melting points. By contrast, amorphous materials have no clearly defined molecular structure and can be described as a super-cooled liquid with an extremely high viscosity such as a viscoelastic "rubber" or a more rigid brittle glass. It is thought that other sugars such as maltose, trehalose, and maltotriose may be included to contribute to the amorphous component. Mannitol may be included to contribute to the crystalline component of the formulation.

The strategy employed to identify a pharmaceutically-acceptable albumin-free formulation of rFVIII was as follows:

(a) The starting material was highly purified rFVIII that was purified using orthogonal chromatographies. These are defined as chromatographic processes which operate under distinct modes and principles and are typically used in succession. As a result, the protein can be rapidly purified through application of different more effective purification methods. This resulted in Factor VIII that was at least 90% pure (by gel electrophoresis) with specific activities greater than 2000 IU/mg protein. Theoretical purity of rFVIII has been a subject of controversy but is thought to be about 3500–5000 IU/mg protein.

(b) The protein was formulated by ultrafiltration/diafiltration (UF/DF) and investigated for recovery across UF/DF, susceptibility to freeze-thaw, and liquid stability under different incubation temperatures.

(c) Potential formulations were further characterized for their thermal behavior by DSC (differential scanning calorimetry). Glass transition temperatures (Tg'), devitrification temperature (Td') and eutectic melting temperature (Te') were determined. This information was used to identify formulations that could be rapidly lyophilized and were targeted for further investigation.

(d) The lead formulations were lyophilized using a rapid freeze drying cycle, and stability analyses were done under standard and accelerated storage temperatures.

(e) Stable formulations were readily identified from samples stored at 40° C. for various time points.

In analyzing the results of numerous studies that led to the formulation of this invention, a multi-variable experimental design strategy and program was used to screen a panel of ingredients that was comprised of mixtures of amino acids salts and sugars. The results were analyzed using a sophisticated program to resolve any interactions between the ingredients, and a multi-variable response-surface analysis of the data was generated. To our surprise, it was found that histidine (commonly used the prior art) actually had a de-stabilizing effect on rFVIII formulations. This led to the need to critically examine the criteria for the various ingredients in the formulation we found was finally acceptable.

EXAMPLE 1

The effect on stability of the lyophilized rFVIII was investigated by titrating various amounts of histidine in a rFVIII mixture comprising 150 mM NaCl, 2.5 mM $CaCl_2$ and 165 mM mannitol. The results are shown below.

TABLE

Percent of initial potency after two weeks/40° C. storage in the presence of histidine.

| Histidine (mM) | % of Initial Activity at 2 weeks/40° C. |
|---|---|
| 20 | 5.9% |
| 55 | 6.3% |
| 75 | 2.5% |
| 100 | 1.9% |

As can be seen from the above data, increasing amounts of histidine resulted in decreased potency of reconstituted lyophilized rFVIII in a dose-dependent fashion. This result suggests that histidine does not play a role in stabilization of FVIII in the lyophilized state.

EXAMPLE 2

Stability of rFVIII in high and low sugar formulations.

Recombinant Factor VIII was prepared in two formulations. Instability was investigated under accelerated storage conditions of 40° C.

The high sugar formulation, similar to that of the prior art, was an amorphous formulation containing, on reconstitution with water, 50 mM of sodium chloride, 2.5 mM of calcium chloride, 5 mM of histidine, and 10% by wt maltose.

The low sugar containing formulation of this disclosure was crystalline with an amorphous component of 1% sucrose (30 mM sucrose) to stabilize the protein. This formulation, on reconstitution with WFI, contained 30 mM of sodium chloride, 2.5 mM of calcium chloride, 20 mM of histidine, 290 mM glycine and approximately 200 IU/mi of rFVIII. This formulation is compared with the prior art formulation in the figure where it can be seen that the low sugar rFVIII formulation of this disclosure is considerably more stable over time than the high sugar stabilized product of the prior art.

Given the above disclosure, it is thought that numerous variations will occur to one skilled in the art. Therefore, it is intended that the above examples should be construed as illustrative only and that the scope of this invention should be limited only by the following claims.

I claim:

1. A stable, albumin-free, lyophilized rFVIII preparation comprising, when reconstituted in water, about 65 to 400 mM glycine, up to 50 mM histidine, 15 to 60 mM sucrose, up to 50 mM NaCl, up to 5 mM $CaCl_2$, and 50 to 1500 IU rFVIII/ml.

2. A stable, albumin-free lyophilized rFVIII preparation comprising, when reconstituted with water, about 290 mM glycine, 20 mM histidine, 30 mM sucrose, 30 mM NaCl, 2.5 mM $CaCl_2$, and 50 to 1500 IU rFVIII/ml.

3. The lyophilized preparation of claim 1 wherein the residual water content is about 1 to 3% by weight.

4. The lyophilized preparation of claim 2 wherein the residual water content is about 1% by weight.

5. A stable, albumin-free, lyophilized rFVIII preparation comprising, when reconstituted in water, about 65 to 400 mM glycine, up to 50 mM histidine, 15 to 60 mM sucrose, up to 50 mM NaCl, up to 5 mM $CaCl_2$, and 50 to 1500 IU rFVIII/ml the preparation being crystalline with an amorphous component and including a residual water content of about 1 to 3% by weight and having the property of being rapidly reconstituted in water.

6. The product of claim 5 wherein the preparation reconstituted in water within 30 seconds.

* * * * *